United States Patent [19]

Gerns

[11] 3,932,542

[45] Jan. 13, 1976

[54] PROCESS FOR PREPARATION OF 2,5-DIBROMO-P-XYLENE

[75] Inventor: Fred R. Gerns, West Lafayette, Ind.

[73] Assignee: Great Lakes Chemical Corporation, West Lafayette, Ind.

[22] Filed: Aug. 26, 1974

[21] Appl. No.: 500,833

[52] U.S. Cl............ 260/650 R; 252/438; 252/440; 252/441
[51] Int. Cl.²......................................... C07C 25/08
[58] Field of Search.................. 260/650 R, 649 DP

[56] References Cited
UNITED STATES PATENTS 3,449,448   6/1969   Kunkel............................ 260/650 R
3,591,645   7/1971   Selwitz........................... 260/649 DP Primary Examiner—D. Horwitz
Attorney, Agent, or Firm—E. Janet Berry; Lawrence Rosen

[57] ABSTRACT

Selective bromination process for 2,5-dibromo-p-xylene which comprises bromination of p-xylene using approximately stoichiometric amounts of bromine and a hydrated iron containing bromination catalyst to give selectively high yields of substantially pure 2,5-dibromo-p-xylene.

12 Claims, No Drawings

PROCESS FOR PREPARATION OF 2,5-DIBROMO-P-XYLENE

The invention is broadly concerned with the selective nuclear bromination of aromatic compounds and more particularly with the isomer selective bromination of p-xylene to produce high yields of very pure 2,5-dibromo-p-xylene substantially without contamination of other dibromo isomers, tribromo-p-xylene or other by-products. The process employs hydrated iron containing bromination catalysts in the presence of a reaction mixture diluent which may be either the intermediate monobromo-p-xylene, a by-product of the bromination reaction itself, and/or a non-reactive inert diluent.

Flame retardant plastics, for example, polyester polymers are currently in great demand in industry and are of particular importance in consumer goods. One of the most commonly used dibasic acids for polyesters is terephthalic acid. A polybrominated terephthalic acid intermediate offers the excellent possibility for providing built-in-flame retardant properties for polyesters. In this approach the polybrominated terephthalic acid enters into the polyesterification reaction and becomes an integral part of the polymer structure, i.e., is a "reactive" flame retardant in the polyester. If offers numerous advantages over the alternate process of using an "additive" flame retardant which is not chemically bound into the polymer structure; specifically, the reactive flame retardant, because it is chemically bound, has a high order of permanence not shared by additive flame retardants which are susceptible to loss by volatilization, by exhudation from the polymer, or by dissolution on laundering or dry cleaning.

Thus dibromoterephthalic acid is a preferred polybasic acid for manufacture of the fire retardant polyesters. The 2,5-dibromoterephthalic acid is the polyacid of choice since it is the most symmetrical of the dibromo isomers and therefore the most preferred as a monomer for polyesters. Any nonsymmetrical products are undesirable and to be avoided since they can participate in the polymerization (polyesterification) reactions and undesirably affect the properties of the polymers. For these reasons, it has been found that an isomer purity of at least about 98% or above is necessary for the 2,5-dibromo-p-xylenes which is to be used for making the dibromoterephthalic acid.

The conversion of the 2,5-dibromo-p-xylene to the corresponding dibromoterephthalic acid is readily accomplished using oxidizing agents known to the art. However, producing 2,5-dibromo-p-xylene of the required purity by an economically feasible and practical process has until discovery of the process disclosed herein been difficult and, in fact, not satisfactory for commercialization.

Experimentally the bromination of p-xylene using conventional catalysts produces monobromo-xylene, isomeric dibromoxylenes and tribromoxylene. The dibromination of p-xylene theoretically produces three isomers, 2,3-dibromo-p-xylene, 2,5-dibromo-p-xylene, and 2,6-dibromo-p-xylene. The 2,5-isomer has been found to be the predominant one formed and the other two isomers are formed in lesser amounts. In fact, the 2,6-isomer is apparently formed only in negligible quantities or not at all. There is, of course, only one tribromo-p-xylene possible.

Although the dibromination theoretically produces three isomeric dibromo-p-xylenes, fortunately the greatest amount is the preferred isomer 2,5-dibromo-p-xylene. Vacuum distillation of the products, while an excellent means for separation of the dibromoxylenes from the mono- and tri-bromo compounds, is an extremely difficult method to use in separating the isomeric dibromo compounds from each other for their vapor pressure are very close.

Variations in bromination conditions in efforts to increase selectivity have been studied extensively. Numerous solvents were examined, among them carbon tetrachloride, methyl cellosolve, methylene chloride and methylcyclohexane. Other catalysts have been tried including iodine, anhydrous ferric bromide, iron, aluminum chloride, and cupric bromide. Also bromine chloride has been tried as a substitute for part or all of the bromine itself as brominating agent.

None of the variations have been found to produce the 2,5-dibromo-p-xylene in yields and selectivities comparable to the process of the invention. Among the disadvantages found in the process variations were dark colored bromination products, difficulties in purification procedures, lack of improvement in selectivity for the desired 2,5-dibromo-p-xylene isomer, and undesirable production of appreciable quantities of tribromoxylene. Formation of tribromoxylene and its presence in the 2,5-dibromo-p-xylene products represents uneconomic waste and creates problems in purification since it cannot be tolerated in the product intended for commercial purposes.

The invention process is a selective and improved dibromination of p-xylene to give almost exclusively 2,5-dibromo-p-xylene as the product. The outstanding feature of the process is the discovery that it is isomer selective and yields relatively pure 2,5-dibromo-p-xylene in high yield with amounts of other brominated products at a minimum; that is, a product is formed which has a high isomer ratio as defined below. To define this term, the isomer ratio, as it is used herein in connection with selectivitity, is the ratio of the 2,5-dibromo-p-xylene isomer to the 2,3-dibromo-p-xylene isomer. For purposes of the process of the invention, an isomer ratio of 13 or 14 or above is considered to be satisfactory.

The essential feature of this newly discovered bromination process is the use of a hydrated iron-containing catalyst. In a preferred embodiment of this process the bromination is carried out in the presence of monobromo-p-xylene, a product of the bromination, as the reaction solvent, or alternatively an inert diluent as the reaction solvent.

Extensive experimental study of the bromination process has shown that the best process for selectivity (i.e., an isomer ratio of 13 or 14 and above) and high yield of 2,5-dibromo-p-xylene depends on operating the bromination process of the invention such that a number of process variables are maintained within critical limits.

It has been found that despite the known art in bromination, the anhydrous iron containing catalysts such as the ferric halides, and more particularly, anhydrous ferric chloride, do not function selectively as catalysts for the bromination of p-xylene to produce high assay 2,5-dibromo-p-xylene. For instance comparison of results obtained with hydrated ferric chloride versus the results using the anhydrous form shows that both selectivity and yield of the desired 2,5-dibromo-p-xylene are unexpectedly and unpredicatably increased by use of the hydrated form of iron-containing catalysts.

Catalyst concentration, i.e. the amount of the hydrated iron containing catalysts employed, is another variable which should be controlled. The catalyst requirement for good results is a small but effective amount of the hydrated catalyst which amount is found in the range of approximately from 0.25 to 5.0 mole percent based on the bromine feed. In any event a sufficient amount of hydrated iron-containing catalyst must be present to function as a catalyst for the dibromination. An excess tends to complicate product recovery and purification procedures and is wasteful.

Control of temperature of the dibromination has been found to be critical in maintaining high isomer ratios. A temperature in the range of about 0° to 40°C. has been found most convenient for practice of the invention although under selected conditions it is possible to use even lower temperatures, for example down to about −20°C., without sacrifice of isomer selectivity. If the temperature is permitted to exceed substantially about 40°C., the isomer ratio drops. If the temperature of the process is allowed to fall below about −5°C., the fluidity of the reaction mixture becomes difficult to maintain and the application of a mechanical blending device becomes necessary. However, within these temperature limits the lower the temperature of bromination, the higher the isomer ratio obtained.

If a diluent is used, it is also important that the bromine to p-xylene molar ratio in the reacting mixture be maintained between 1.8 and 2.4. Too little bromine gives decreased amounts of 2,5-dibromo-p-xylene while a too high ratio of bromine to p-xylene is unnecessary and is wasteful of bromine, thereby creating process and product difficulties.

Catalyst studies on the process include the use of cobalt bromide both anhydrous and the hexahydrate, manganese bromide anhydrous and the tetrahydrate, anhydrous nickel bromide, anhydrous zinc bromide, molybdenum pentachloride, both anhydrous and the pentahydrate, and aluminum chloride. In general, a multiplicity of brominated products was obtained, showing both poor isomer ratios, and either too sluggish or too vigorous bromination activity. For instance molybdenum pentachloride pentahydrate required more than twice the reaction time as did the preferred hydrated iron containing catalyst.

It has been found that hydrated ferric halides are the preferred catalysts. Unexpectedly, the hydrated ferric salts function far better than the anhydrous forms. A trihydrate of ferric halide seems to be an optimum and preferred level of hydration, although the degree of hydration may range from 2 to 6. A lower level of hydration gives lower isomer ratios and/or a higher level of tribromination, while greater amounts of water appear to promote formation of high boiling material. The appropriate hydrated form can be supplied per se to the reaction or it can be prepared in situ by addition of the appropriately equivalent amounts of anhydrous ferric chloride or bromide and partially hydrated material and/or water to the reaction mixture. The hydrated form of ferric halide catalyst can also be conveniently supplied by catalyst recycle from previous runs. Ferric chloride trihydrate can be prepared either by preliminary mixing of equivalent amounts of the anhydrous and hexahydrate forms or can be prepared in situ.

It is an advantage of a preferred embodiment of the invention process that it is possible to obtain yields of 85% or higher of 2,5-dibromo-p-xylene of very high purity (above 98%). It is possible to isolate the reaction product 1) by distillation which first removes the monobromo-p-xylene and then the dibromo-p-xylenes, or 2) by washing the reaction mixture, then stripping off the monobromo-p-xylene. As an additional feature of this invention, it has been found possible to purify further the isolated product whose dibromoxylene content is at least about 92% 2,5-dibromo isomer and to obtain material of over 99% purity by selective dissolution at ambient temperature of the impurities from the 2,5-dibromo-p-xylene using for instance a lower molecular weight aliphatic alcohol of 1–4 carbon atoms, such as methanol, ethanol, isopropanol, n-propanol, butanols, and mixtures thereof. This purification step removes residual small amounts of monobromo-p-xylene, the 2,3-dibromo isomer and trace amounts of high boiling materials.

Thus, using the preferred process of the invention in which the intermediate monobromo-p-xylene essentially acts as a reaction mixture diluent, fully recoverable under the appropriately selective conditions, and using hydrated ferric halide as the bromination catalyst there is obtained a product whose dibromo-p-xylene content is 92–96% 2,5-isomer and which contains essentially no tribromo-p-xylene. It is contemplated as a preferred embodiment of the invention that xylene and bromine are charged to the reaction vessel which contains a monobromo-p-xylene heel and catalyst. In a continuous embodiment p-xylene, bromine, and catalyst are continually fed to a mixture of the reactants and the monobromo-p-xylene with continuous removal of hydrogen bromide and product. Obviously, other variants of the feed streams for continuous operation are possible. It is also possible to carry out the process of the invention by substituting a part or all of the intermediate monobromo-p-xylene by an appropriate amount of a reaction mixture diluent which is substantially unreacting under the conditions of the bromination reaction. Diluents which can be used include halogenated solvents such as carbon tetrachloride, chloroform, methylene chloride, mixed chlorinated solvents, methylcyclohexane, and higher boiling aliphatic hydrocarbons.

It has been further found that the use of hydrated ferric chloride catalysts for bromination actually suppresses tribromination of the p-xylene, thereby assuring the obtaining of a pure dibromo derivative as the principal product.

The process of the invention has been found to proceed well when carried out both in batch or semi-continuous operations and is especially adaptable to operate as a continuous process.

The invention will be illustrated in greater detail by the examples presented hereinbelow. It is not intended however to limit the invention in any way specifically thereto.

EXAMPLE 1

Dibromination of p-Xylene with Hydrated Ferric Chloride Catalyst p-Xylene (212 grams, 2.0 moles) and 7 grams of ferric chloride hexahydrate (0.026 moles, 1 mole percent based on bromine) were charged to a 500 ml. four-neck flask. To this mixture, while maintaining stirring and a temperature of 25°C. there was added from a dropping funnel, 416 g. (2.6 moles) bromine. The addition of bromine required 2¾ hours after which the mixture was allowed to stir an additional hour at 20°–25°C.

Samples of the reaction mixture were taken at intervals during the reaction (2.0 moles bromine, 2.15 moles bromine, 2.3 moles bromine, 2.45 moles bromine, and 2.6 moles bromine). These samples were analyzed by vapor phase chromatography and the average isomer ratio as defined above was found to be 17. The product, 2,5-dibromo-p-xylene was identified by vapor phase chromatography.

EXAMPLE 2

Batch Process Dibromination of p-Xylene

A bromination reaction was carried out according to the process of the invention wherein 625 g. (6.15 moles) of p-xylene and 12.95 g. (0.08 mole) of anhydrous ferric chloride and 4.3 g. (0.24 mole) deionized water (to produce $FeCl_3.3H_2O$ in situ) were added to a stirred reaction vessel, fitted with a thermometer and condenser with gas outlet to a water trap. Bromine (1280 g., 8.0 moles) was added to the stirred mixture of p-xylene and catalyst, initially held at 10°–15°C. (first 15% of bromine addition) then at 0°–5°C. Hydrogen bromine was collected in the water trap. After all the bromine had been added, stirring was continued for 1 hour at 0°–5°C., then at ambient temperature until hydrogen bromide evolution ceased. A total of 388.3 g. hydrogen bromide (90% theory) was collected.

The product may be washed with caustic and/or water as desired, and the monobromo-p-xylene stripped off. The washing steps are not, however, necessary. The washed and stripped product is substantially pure. In this instance, however, the reaction mixture was distilled without washing using a packed column at reduced pressure. After removal of the monobromo-p-xylene the column was replaced by a still head and the main product fraction distilled via a short path.

The monobromo-p-xylene fraction obtained as a forerun boiled in the range 75°–80°C. at 8 mm. pressure. The product fraction distilled at 119°–123°C. at 8 mm. pressure. The product fraction consisted of 473 grams of a white crystalline solid assaying 93.4% of 2,5-dibromo-p-xylene. The isomer ratio was found to be 16.1. The distillation residue consisted of the iron catalyst and a small amount of tar.

EXAMPLE 3

Semi-Continuous Dibromination with Recycle of Monobromo-p-Xylene

This experiment was carried out in two successive steps. In the first stage the total p-xylene was divided into two parts and one-half of the p-xylene was added to the reaction vessel with the catalyst. The other half of the p-xylene and the bromine were then added simultaneously but in separate streams to the flask while maintaining the temperature of the reacting mixture at 20°–25°C. When the reaction was completed as evidenced by no further hydrogen bromide evolution, the resulting mixture was distilled. An initial fraction of monobromo-p-xylene was taken off at 75°–103° (9mm). The 2,5-dibromo-p-xylene was recovered by distillation at 122°–126° (10 mm) as a water-white liquid which solidified to a white, fused, crystalline mass.

In the second stage p-xylene was brominated using recovered and recycled monobromo-p-xylene from the above described first step as diluent. The monobromo-p-xylene and catalyst were charged to a reaction vessel and bromine and p-xylene then added simultaneously to the reaction flask at 20°–25°C. When reaction was completed, the mixture was distilled as described before.

a. A total of 212 g (2.0 moles) p-xylene of 99 mole % purity was used. The reaction vessel was charged with 106 g. of the p-xylene and as catalyst 2.43 g. (0.015 mole) anhydrous ferric chloride and 4.05 g. (0.015 mole) ferric chloride hexahydrate to give the preferred ferric chloride trihydrate as catalyst in the reaction vessel. p-Xylene (106 g.) and 480 g. (3.0 moles) of bromine were added simultaneously but separately to the reaction mixture at a rate such that their additions were completed at the same time. The reaction temperature was maintained at 20°–25°C. by cooling. Hydrogen bromide (224 g. — 92% of theoretical) was evolved. The resulting reaction mixture was a thick brown slurry. After hydrogen bromide evolution ceased, the mixture was heated to 40°–45°C. to dissolved the solids in order to facilitate transfer of the mixture. The reaction mixture was distilled through a packed vacuum-jacketed column to strip off the monobromo-p-xylene. The column was then replaced with a still head and the main product fraction, 2,5-dibromo-p-xylene, distilled via short path.

The monobromo-p-xylene fraction was collected over the range of 75°–103°C. at 9 mm. pressure. The product fraction 2,5-dibromo-p-xylene distilled at 122°–126°C. at 10 mm. pressure and weighed 233.7 and assayed at 94.4%. The isomer ratio was 17.

b. Monobromo-p-xylene (185 g., 1.0 mole) prepared as described above, was charged to a reaction flask together with 1.475 g. (0.0091 mole) of anhydrous ferric chloride and 2.46 g. (0.0091 mole) of ferric chloride hexahydrate. p-Xylene (96.3 g. 0.91 mole) and 291 g. (1.82 moles) of bromine were added simultaneously but separately to the reaction mixture at a rate such that the additions were completed at the same time. The reaction mixture was maintained at 20°–25°C. with cooling. As described in part (a) above, hydrogen bromide was evolved and a brown slurry was formed. A total of 130 g. (88.2% of the theoretical) hydrogen bromide was evolved. The reaction mixture was distilled and the products recovered in a similar fashion as described in part (a) above. The results obtained are as follows.

In this reaction, a product fraction boiling at 123°–124°C. at 10 mm. pressure was collected. This 210.7 g. of product assayed 93.4% 2,5-dibromo-p-xylene and the isomer ratio was 14.4.

EXAMPLE 4

Dibromination Process Using Trihydrate of Ferric Chloride

Monobromo-p-xylene (472 g., 2.55 moles) and catalyst, 3.29 (0.0203 mole) anhydrous ferric chloride and 4.58 g. (0.0203 mole) ferric chloride hexahydrate were charged to the stirred reaction vessel. p-Xylene (215 grams, 2.03 moles) and 648 g. (4.06 moles) bromine were added simultaneously but separately at 0°–5°C. with cooling for a period of four hours. The temperature was allowed to rise to 25°C. At the end of the reaction period the temperature was raised to 40°C. to dissolve all solids and facilitate transfer. The unwashed reaction mixture was distilled under reduced pressure of 10 mm. A fraction consisting of monobromo-p-xylene was collected at 70°–85° and an intermediate cut was recovered at 85°–119°. The product 2,5-dibromo-p-xylene was distilled at 119°–126°C. and recovered as a water white liquid which crystallized on cooling to a white solid. The results obtained are summarized below.

A. Summary of Distillation

| Fraction No. | Head temp. °C. | p. mm. | Wt. g. |
|---|---|---|---|
| 1 | 70–85 | 10 | 485* |
| 2 | 85–119 | 10 | 5.5 |
| 3 | 119–126 | 10 | 516.2 |
| Pot Residue | — | — | 14.3 |
| Recovered from column | — | — | 5.0 |

*As in other examples presented herein, this figure includes the water from the catalyst codistilled. It can be easily and completely decanted from the organic fractions.

B. VPC Assays (Area %)

| Sample No. | p-xylene | monobromo p-xylene | 2,5-DBX* | 2,3-DBX | Isomer ratio |
|---|---|---|---|---|---|
| Reaction mixture | 0.02 | 52.6 | 45.6 | 1.81 | 25.2 |
| Forerun | 0 | 99.4 | 0.53 | — | — |
| Middle cut | 0 | 47.0 | 51.6 | 1.1 | 47 |
| Product cut | 0 | 0.13 | 95.9 | 4.0 | 24 |

*DBX = dibromo-p-xylene

C. HBr Recovery

|  | % of Theoretical (329 g) Collected in Water Trap |
|---|---|
| At end of Br$_2$ addition | 85.6 |
| At end of 0–5°C. stirring period | 87.8 |
| At end of 25°C. stirring period | 90.6 |
| At 40° (transfer temperature) | 91.2 |

D. Yield of Dibromo-p-Xylenes

Theoretical yield of DBX = 2.03 moles on bromine and p-xylene
= 2.03 (264) = 535 g.
Yield of DBX (all fractions) = 516.2 g.
Actual % yield on p-xylene and bromine = 96.5%

EXAMPLE 5

Continuous Plant Process

Preparatory to a continuous run a "heel" was prepared in a 10 gal. reactor by adding over a period of 1.75 hours, 128 lbs. of bromine to 60 lbs. of p-xylene and 25 oz. of the preferred catalyst while maintaining a temperature of 15°–19°. After completion of bromine addition, the system was held with agitation for an additional hour. The system was then ready for the continuous run.

There were three feed streams employed in the continuous process. These were bromine, catalyst, and a premixed stream of p-xylene and a recycle fraction consisting substantially of monobromo-p-xylene.

Catalyst, 32 oz., was charged to the reactor on an intermittent basis every 15 minutes throughout the period of the run.

p-Xylene, 49 lbs., was mixed with 160 lbs. of a recycle fraction assaying 92% monobromo-p-xylene. A 204 lb. portion of this mixture was fed simultaneously with 152 lbs. of bromine to the reactor over a period of 4.25 hours.

The temperature was maintained at 14°–26° during the reaction by varying the brine flow through the cooling jacket. Product coming from the reactor was passed through a small heat exchanger, warmed to about 50°C. and collected in a receiver. The crude reaction mixture in the receiver was then neutralized by multiple contacts with deionized water. Light ends were then distilled off at a reduced pressure of 10–20 mm.

The dibromo-p-xylene product remaining in the pot was then fed in the molten state into an agitated reactor containing methanol at ambient temperature. After agitation for about one hour the product was filtered off. The product obtained at this stage had the desired isomer purity of > 98% 2,5-isomer. For removal of color, a single plate overhead flash distillation of methanol-wet filter cake was utilized. Overall yields were comparable to those achieved on laboratory scale.

|  | Product Assay (VPC, area %) | | | | |
|---|---|---|---|---|---|
|  | p-Xylene | Mono-bromo p-xylene | 2,5-Dibromo-p-xylene | 2,3-Dibromo-p-xylene | Isomer Ratio |
| Washed crude reaction mixture | 0.86 | 56.1 | 41.1 | 1.88 | 21.9 |
| Crude product after removal of light ends | tr | 7.2 | 89.6 | 3.2 | 28.0 |
| Product after methanol slurry | — | .4 | 99.1 | .5 | 198. |

EXAMPLE 6

Effects of Various Iron Containing Catalysts on Dibromination of p-Xylene

A series of experimental bromination reactions was carried out using various iron containing catalysts and a molar ratio of bromine to p-xylene of 1.3. The reaction temperature used was 0°–5°C. with the first 15% of bromine being added at 10°–15°C. to facilitate agitation of the reaction mixture during the initial stages of the bromination. No extraneous solvent was employed. The concentration of the respective catalysts employed is in each case, expressed as mole percent on bromine used. In each case, the reaction mixture was washed with 10% sodium hydroxide. The experimental results are shown in Table I presented below:

TABLE 1

Comparison of Various Iron Catalysts in Dibromination of p-Xylene

| Run No. | Catalysts | Conc. Mole % based on $Br_2$ | p-Xylene | Mono-bromo-p-xylene | 2,5-Dibromo-p-xylene | 2,3-Dibromo-p-xylene | 2,5-/2,3- Isomer Ratio | Tribromo-p-xylene | High Boilers |
|---|---|---|---|---|---|---|---|---|---|
| 1 | $FeCl_3$ | 1 | 2.31 | 60.0 | 33.3 | 4.13 | 8.1 | 0.21 | 0.04 |
| 2 | $FeCl_3 \cdot 3H_2O$ | 1 | 0 | 66.7 | 31.4 | 1.69 | 18.6 | 0 | 0.07 |
| 3 | $FeCl_3 \cdot 6H_2O$ | 1 | 0 | 64.4 | 32.1 | 1.27 | 25.3 | 0 | 2.3 |
| 4 | $FeBr_3$ | 1 | 0.58 | 62.3 | 33.0 | 4.13 | 8.0 | 0.01 | Trace |
| 5 | $FeBr_3$ $I_2$ | 1 0.1 | 0.24 | 62.6 | 32.6 | 4.22 | 7.7 | 0.17 | Trace |
| 6 | Fe powder | 1.2 | 0.18 | 65.56 | 30.35 | 3.69 | 8.2 | 0 | 0 |
| 7 | Fe powder $I_2$ | 1.2 0.063 | 0.46 | 70.26 | 25.85 | 3.35 | 7.7 | 0 | 0 |
| 8 | Fe filings $I_2$ | 1.2 0.063 | 0.1 | 65.94 | 30.18 | 3.80 | 7.9 | 0 | 0 |

These experimental data show the unexpected superiority of the hydrated iron containing catalysts of the invention used in Runs 2 and 3 for producing high purity 2,5-dibromo-p-xylene as compared with results from other closely related iron-containing catalysts. Runs 1 and 4 using anhydrous ferric halides show low isomer ratios. Addition of iodine, a well-known bromination catalyst to the ferric halide in Run 5 did not improve the poor selectivity of the anhydrous ferric halide catalyst. Iron powder alone, or with iodine as well as iron filings with iodine, show similar poor isomer selectivities as dibromination catalysts (Runs 6, 7, and 8), i.e., show low isomer ratios.

EXAMPLE 7

Effect of Degree of Hydration of Catalyst a. A series of bromination experiments was carried out in which p-xylene was subjected to bromination using anhydrous ferric chloride as well as variations in the hydrated forms of the salt (from 1 ½ to 6 moles of water per mole of ferric chloride). The reaction charge was 212 g. (2.0 moles) p-xylene, 416 g. (2.6 moles) bromine and 0.026 moles of catalyst. The results are shown below in Table II. The catalyst concentration was 1 mole % based on the bromine used. No extraneous solvent was employed. The bromine to p-xylene ratio was maintained at 1.3 in all experiments and the temperature was 0°–5°C. To facilitate stirring a higher temperature of about 15°C. was employed in the initial stages of the reaction period. The individual reaction mixtures were washed with 10% sodium hydroxide.

TABLE II

Effect of Hydration on Ferric Chloride Catalysis of Dibromination
Crude Reaction Mixture Assay VPC (area %)

| Run No. | Catalyst | p-xylene | Mono-bromo-p-xylene | 2,5-Dibromo-p-xylene | 2,3-Dibromo-p-xylene | 2,5-/2,3- Isomer Ratio | Tribromo-p-xylene | High Boilers |
|---|---|---|---|---|---|---|---|---|
| 9 | $FeCl_3$ | 2.31 | 60.0 | 33.3 | 4.13 | 8.1 | 0.21 | 0.04 |
| 10 | $FeCl_3 \cdot 1½H_2O$ | 15.0 | 32.1 | 46.0 | 5.10 | 9.0 | 1.80 | — |
| 11 | $FeCl_3 \cdot 2H_2O$ | 0 | 68.0 | 29.8 | 2.21 | 13.5 | Trace | Trace |
| 12 | $FeCl_3 \cdot 3H_2O$ | 0 | 66.68 | 31.4 | 1.69 | 18.6 | 0 | 0.07 |
| 13 | $FeCl_3 \cdot 4½H_2O$ | 0 | 66.0 | 31.9 | 1.8 | 17.7 | 0 | 0.86 |
| 14 | $FeCl_3 \cdot 6H_2O$ | 0 | 64.4 | 32.1 | 1.27 | 25.3 | 0 | 2.3 | b. In similar way a series of dibromination reactions was carried out using recycle monobromo-p-xylene as diluent with anhydrous ferric chloride and variations in the hydrated forms of the salt (from 1 ½ to 12 moles of water per mole of ferric chloride). In each case, the catalyst was used in an amount of 1 mole % based on bromine used. The results are shown in Table III below. The mole ratio of recycled monobromo-p-xylene to p-xylene was 1.25 and the mole ratio of bromine to p-xylene was 2.0. The reaction mixtures were each worked with 10% sodium hydroxide.

TABLE III

Effect of Hydration on Ferric Chloride Catalysis of Dibromination
Reaction Mixture Assay VPC (area %)

| Run No. | Catalyst $FeCl_3 \cdot xH_2O$ x | % Theoretical HBr collected when all $Br_2$ added | p-xylene | Mono-bromo p-xylene | 2,5-Dibromo-p-xylene | 2,3-Dibromo-p-xylene | 2,5/2,3- Isomer ratio | tribromo p-xylene | High No. | Boilers % |
|---|---|---|---|---|---|---|---|---|---|---|
| 15 | 0 | 89 | 3.84 | 44.1 | 46.7 | 5.14 | 9.1 | 0.6 | 1 | 0.06 |
| 16 | 1½ | 86 | 2.20 | 45.8 | 46.3 | 5.49 | 8.4 | 0.10 | 0 | — |
| 17 | 2 | 87 | 0.41 | 50.9 | 45.4 | 3.24 | 14.0 | tr | — | tr |
| 18 | 2½ | 88 | 0.81 | 50.5 | 45.9 | 2.73 | 16.8 | 0 | — | tr |
| 19 | 3 | 87.7 | 0.66 | 50.9 | 46.0 | 2.27 | 20.3 | 0.05 | — | tr |
| 20 | 4½ | 83 | tr | 52.2 | 45.7 | 2.02 | 22.6 | tr | — | tr |
| 21 | 6 | 76 | 0.14 | 51.9 | 42.6 | 2.33 | 18.5 | tr | 6 | 3.4 |
| 22 | 9 | 55 | tr | 52.9 | 44.1 | 2.71 | 16.3 | 0.03 | 5 | 0.3 |
| 23 | 12 | 50 | tr | 55.8 | 41.1 | 2.13 | 19.3 | tr | 7 | 2 |

These experiments indicate that the degree of hydration of the catalyst governs the isomer selectivity or the relative distribution of the bromine atoms on the aromatic nucleus of the p-xylene. Clearly the anhydrous ferric chloride is unsatisfactory in that the isomer ratio obtained is low.

the catalyst with simultaneous addition of bromine and p-xylene to recycle monobromo-p-xylene as solvent. The bromo-p-xylene to p-xylene molar ratio was 1.25 and the bromine to p-xylene molar ratio was 2.0.

TABLE V

Effect of Temperature in Dibromination of p-Xylene
Reaction Mixture Assay
VPC (area %)

| Run No. | Reaction Temp. | % HBr Collected | p-Xylene | Mono-bromo-p-xylene | 2,5-Dibromo-p-xylene | 2,3-Dibromo-p-xylene | 2,5–/2,3- Isomer Ratio | High Boilers |
|---|---|---|---|---|---|---|---|---|
| 29 | 0–5° | 87.5 | 0.66 | 50.9 | 46.0 | 2.27 | 20.3 | 0.05 |
| 30 | 20–25 | 88.5 | 0.60 | 51.2 | 45.7 | 2.66 | 17.2 | Trace |
| 31 | 30–35 | 89 | 0.42 | 52.0 | 44.2 | 2.87 | 15.4 | 0.5 |
| 32 | 40–45 | 92 | 0.47 | 50.2 | 44.8 | 4.31 | 10.4 | Trace |
| 33 | 50–55 | 92 | 2.48 | 48.8 | 43.6 | 5.16 | 8.4 | Trace |

EXAMPLE 8

Effect of Variation in $FeCl_3 \cdot 3H_2O$ Catalyst Concentration

A series of runs was carried out to study the effect of variations of concentration of the $FeCl_3 \cdot 3H_2O$ catalyst from 0.25 to 5.0 mole % based on the bromine. The experiments were performed as a semi-continuous recycle process in which there was simultaneous addition of bromine and p-xylene in a molar ratio of 2.0 to the recycle stream of monobromo-p-xylene and catalyst. The bromination temperature was 0°–5°C. and the reactions times were constant for each experiment. The results are shown in Table IV below. These data indicate that the catalyst concentrations of the hydrated iron containing catalysts can vary from about 0.25 up to 5.0 mole % with satisfactory results, i.e., to yield products of high isomer ratios.

These data show that temperatures of about 0°C. up to about 40°C. are satisfactory for carrying out the process of the invention. Temperatures in the range of 40°–45°C. and also up to the range of 50°–55°C. show a decrease in isomer ratio and the amount of high molecular weight by-products (high boiling fraction) tends to increase somewhat at these higher temperatures. At the lower temperatures of the useful range (below 0°C.) the isomer ratio is increased but fluidity of the reaction mass decreases to the point where proper agitation of the mixture can no longer be effected by using conventional stirring means and mechanical blending devices are necessary to accomplish the desired intimate mixing of the reactants.

EXAMPLE 10

Effect of Variation of Monobromo-p-xylene to p-Xylene ratio

A series of experiments was carried out to determine the effect of varying the ratio of monobromo-p-xylene

TABLE IV

Effect of Variation in $FeCl_3 \cdot 3H_2O$ Concentration
Reaction Mixture Assay
VPC (Area %)

| Run No. | Catalyst Conc. | % HBr Collected | p-xylene | Mono-bromo-p-xylene | 2,5-Dibromo p-xylene | 2,3-Dibromo-p-xylene | 2,5–/2,3- Isomer Ratio | High Boilers |
|---|---|---|---|---|---|---|---|---|
| 24 | 0.25 | 78.0 | 0.02 | 53.7 | 43.6 | 2.64 | 16.5 | Trace |
| 25 | 0.5 | 86.0 | 0.1 | 51.8 | 45.7 | 2.78 | 20.1 | Trace |
| 26 | 1.0 | 88 | 0.66 | 50.9 | 46.0 | 2.27 | 20.3 | 0.05 |
| 27 | 2.5 | 84.1 | 1.10 | 50.8 | 46.1 | 1.93 | 23.9 | 0.03 |
| 28 | 5.0 | Leak in trap | 0.24 | 52.1 | 45.3 | 2.34 | 19.4 | trace |

EXAMPLE 9

Effect of Temperature Variations

The effect of reaction temperature as a variable in the bromination reaction in the preferred range of 0°–40°C. was studied in a series of experiments. The results obtained are set forth in Table V below. The experiments were all carried out using $FeCl_3 \cdot 3H_2O$ as to p-xylene. In all the reactions $FeCl_3 \cdot 3H_2O$ was used as the catalyst and temperatures were maintained at 0°–5°C. The experimental runs are summarized in Table VI below.

These experiments show that molar ratios of monobromo-p-xylene to p-xylene in the range of about 1 to 3 and molar ratios of monobromo-p-xylene to bromine in the range of about 0.5 to 1.5 are satisfactorily and operable in the process, i.e., yield products of high isomer ratios.

TABLE IV

| Run No. | Monobromo-p-xylene p-xylene ratio molar | | Monobromo-p-xylene/ bromine ratio molar | | Mono-bromo-p-xylene | VPC - Assay (area %) 2,5-Dibromo-p-xylene | 2,3-Dibromo-p-xylene | Isomer Ratio | High boiling fraction |
|---|---|---|---|---|---|---|---|---|---|
| | molar | wt. | molar | wt | | | | | |
| 34* | 1.0 | 1.75 | 0.5 | 0.58 | 70.2 | 28.17 | 1.50 | 18.8 | 0 |
| 35 | 1.26 | 2.2 | 0.63 | 0.73 | 51.6 | 45.9 | 2.46 | 18.6 | 0 |
| 36 | 1.9 | 3.3 | 0.94 | 1.1 | 60.44 | 36.80 | 2.57 | 14.3 | 0 |

TABLE IV-continued

| Run No. | Monobromo-p-xylene ratio molar | wt. | Monobromo-p-xylene/ bromine ratio molar | wt | Mono-bromo-p-xylene | VPC - Assay (area %) 2,5-Dibromo-p-xylene | 2,3-Dibromo-p-xylene | Isomer Ratio | High boiling fraction |
|---|---|---|---|---|---|---|---|---|---|
| 37 | 2.78 | 4.85 | 1.39 | 1.6 | 69.6 | 28.8 | 1.60 | 18.0 | 0 |

*Reaction mixture became unstirrable using a conventional laboratory stirrer after 76% of bromine had been added.

EXAMPLE 11

Effects of Excess Bromine

A series of semi-continuous experiments was run using recycle monobromo-p-xylene as the diluent. The catalyst was $FeCl_3 \cdot 3H_2O$ and bromination temperature was 20°–25°C. The monobromo-p-xylene to p-xylene molar ratio was 1.25. The results of these experiments are shown in Table VII below.

It was found from these experiments that the use of up to about a 10% excess (over the stoichiometric) amount of bromine does not result in any significant increase of more highly brominated xylenes.

TABLE VII

Effect of Increase in Bromine over Stoichiometric Amount
Crude Reaction Mixture VPC-assay (Area %)

| Run No. | Bromine-p-xylene Mole Ratio | p-Xylene | Mono-bromo-p-xylene | 2,5-Dibromo-p-xylene | 2,3-Dibromo-p-xylene | 2,5-/2,3- Isomer Ratio | Dibromo-Monobromo Ratio | High Boilers |
|---|---|---|---|---|---|---|---|---|
| 38 | 2.0 | 0.60 | 51.2 | 45.5 | 2.66 | 17.1 | 0.94 | Trace |
| 39 | 2.1 | 0.36 | 47.5 | 49.5 | 2.69 | 18.4 | 1.1 | Trace |
| 40 | 2.2 | 0.08 | 43.0 | 53.8 | 3.04 | 17.7 | 1.32 | 0.1 |

EXAMPLE 12

Effects of Variations in Use of Inert Diluents

A series of experimental reactions was carried out in which various inert diluents which were substantially non-reactive under the reaction conditions were tested and evaluated for selectivity as compared with use of the intermediate, monobromo-p-xylene as diluent. The bromine to p-xylene ratio was 2.0. A temperature of about 0°C. was employed; the reaction mixture was held at 10°–15°C. during addition of the first 15% of the bromine to facilitate agitation of the reaction mixture during the initial stages of bromination. The catalyst employed in each case was $FeCl_3 \cdot 3H_2O$. In each case the resulting reaction mixture, was washed with 10% sodium hydroxide. The inert, non-reactive diluents were in each case, Run Nos. 42, 43, 44, and 45, found to be equal to monobromo-p-xylene as diluents.

TABLE VIII

Variations in Diluent Used
Reaction Mixture Assay (VPC, area %)

| Run No. | Diluent | % HBr Collected | 2-Bromo-p-xylene | 2,5-Dibromo-p-xylene | 2,3-Dibromo-p-xylene | 2,5-/2,3- Isomer Ratio | Tribromo-p-xylene |
|---|---|---|---|---|---|---|---|
| 41 | Monobromo-p-xylene | 88 | 50.9 | 46.0 | 2.27 | 20.3 | 0.05 |
| 42 | Carbon Tetrachloride | 84 | 3.43 | 93.0 | 3.16 | 29.4 | 0.2 |
| 43 | Chloroform | 69.4 | 7.69 | 88.4 | 3.93 | 22.5 | Trace |
| 44 | Methylene Chloride | 83.9 | 1.48 | 93.0 | 5.00 | 18.6 | 0.3 |
| 45 | methyl Cyclohexane | 84.2 | 5.06 | 91.08 | 3.51 | 25.9 | 0.3 |

EXAMPLE 13

Comparative Bromination Studies Using Iron Containing Compounds as Catalysts A series of comparable runs was carried out using various iron-containing compounds as catalysts for the dibromination reaction. Generally, both the anhydrous and the corresponding hydrated forms of the iron-containing compounds were used. Monobromo-p-xylene was employed as the diluent and the bromine to p-xylene ratio was 2.0.

The reactant charge was as follows:
106 g. (1.0 mole) p-xylene
320 g. (2.0 moles) bromine
231 g. (1.25 moles) monobromo-p-xylene
0.02 mole catalyst The bromine and p-xylene were added simultaneously to the reaction vessel. The reaction temperature was 0°C., with a temperature of 10°–15°C. being maintained during the addition of the first 15% of the bromine to facilitate agitation of the reaction mixture during the initial stages of the bromination. The final reaction mixture in each Run was washed with 10% sodium hydroxide. These runs show the increased effectiveness of hydrated iron containing catalysts over their anhydrous counter-parts.

TABLE IX

CATALYSTS BY ANHYDROUS AND HYDRATED IRON CONTAINING SALTS
Reaction Mixture Assay (VPC area %)

| Run No. | Catalyst | % HBr Collected | p-xylene | 2-bromo-p-xylene | 2,5-Dibromo-p-xylene | 2,3-Dibromo-p-xylene | 2,5/2,3- isomer ratio | Tribromo-p-xylene | High Boilers No. | % |
|---|---|---|---|---|---|---|---|---|---|---|
| 46 | $FeCl_3$ | 89 | 3.84 | 44.1 | 46.7 | 5.14 | 9.1 | 0.6 | 1 | 0.06 |
| 47 | $FeCl_3 \cdot 3H_2O$ | 88 | 0.66 | 50.9 | 46.0 | 2.27 | 20.3 | 0.05 | — | tr |
| 48 | $FeBr_3$ | 90 | 17.5 | 22.9 | 50.9 | 3.86 | 13.2 | 4.85 | 1 | 0.8 |
| 49 | $FeBr_3 \cdot 3H_2O$ | 89 | 1.99 | 48.8 | 45.8 | 3.37 | 13.6 | tr | 0 | 0 |

TABLE IX-continued

CATALYSTS BY ANHYDROUS AND HYDRATED IRON CONTAINING SALTS

| Run No. | Catalyst | % HBr Collected | p-xylene | 2-bromo-p-xylene | 2,5-Dibromo-p-xylene | 2,3-Dibromo-p-xylene | 2,5/2,3-isomer ratio | Tribromo-p-xylene | High Boilers No. | High Boilers % |
|---|---|---|---|---|---|---|---|---|---|---|
| 50 | $FePO_4$ | 86.7 | 0.10 | 51.5 | 45.3 | 3.08 | 14.7 | 0 | 2 | 0.15 |
| 51 | $FePO_4.3H_2O$ | 73 | 0 | 53.8 | 42.2 | 2.42 | 17.4 | 0 | 4 | 1.7 |
| 52 | $Fe(NO_3)_3.9H_2O$ | 33.3 | 0 | 50.8 | 46.6 | 2.55 | 18.3 | 0 | — | tr |
| 53 | $Fe_2(SO_4)_3$ | 81.5 | 1.99 | 48.2 | 44.9 | 4.87 | 9.3 | 0 | — | tr |
| 54 | $Fe_2(SO_4)_3.3H_2O$ | 83 | 0.41 | 50.6 | 46.2 | 2.64 | 17.5 | 0 | 3 | 0.16 |
| 55 | $Fe_2O_3$ | 87.8 | 4.07 | 42.7 | 47.2 | 5.81 | 8.1 | 0.19 | 0 | 0 |
| 56 | $Fe_2O_3.3H_2O$ | 85.2 | 0.3 | 50.2 | 41.3 | 1.75 | 23.6 | tr | 6 | 6.5 |
| 57 | $FeCl_2.4H_2O$ | 87.5 | 0.15 | 52.1 | 44.4 | 1.5 | 29.6 | 0 | 5 | 1.7 |
| 58 | $FeSO_4$ | 89 | 1.65 | 49.3 | 44.6 | 4.46 | 10 | 0 | 0 | 0 |
| 59 | $FeSO_4.3H_2O$ | 71 | tr | 54.6 | 39.0 | 2.86 | 13.6 | 0 | 4 | 3.5 |
| 60 | Fe powder | 90.5 | 2.13 | 48.1 | 45.3 | 4.48 | 10.1 | 0 | 0 | 0 |
| 61 | Fe powder.$3H_2O$ | 86.5 | 0.34 | 47.4 | 43.3 | 1.84 | 23.5 | tr | 8 | 7 |

EXAMPLE 14

Comparative Process Studies Between the Invention Process and Conventional Bromination Process In order to compare as directly as possible the conventional bromination process with the process of the invention the data of the following Table X is presented:

TABLE X

| Experiment | A Invention Process | B Typical "Conventional" Process |
|---|---|---|
| Catalyst (1 mole% on $Br_2$) | $FeCl_3.3H_2O$ | $FeCl_3$ (anhyd.) |
| Solvent | recycle monobromo xylene | $CCl_4$ |
| Theoretical dibromoxylene/solvent Productivity | 150 g/100 ml | 100 g/100 ml |
| Reaction Temperature | 20–25°C. | 10–15°C. |
| $Br_2$ excess | 0 | 0 |
| Yield (distilled) | 96% on xylene and $Br_2$ | 82% on $Br_2$ 86% on xylene |
| 2,5-DBX/2,3-DBX ratio | 15–18 | 8 |
| 2,5-DBX assay | 92–95% | 86.6% |
| tribromo-p-xylene | 0 | 1.0% |

Experiment A shows typical results obtained by using the process of the invention as described for instance in Example 3(b) above.

Experiment B was carried out using a typical (conventional) bromination process. To a reaction vessel containing 106 g. p-xylene (1.0 mole) 260 ml. $CCl_4$, 3.24 g. (0.02 mole) anhydrous ferric chloride there was added 320 g. (2.0 moles) bromine over a period of 2 hours. Temperature was maintained at 0°–5°C. After an additional 1½ hour of stirring, the reaction mixture was sampled for vapor phase chromatography. The reaction mixture was worked up substantially as that of Experiment A.

The yields reported represent the total amount of dibromoxylenes collected overhead in the fractionation and do not include the amounts of material residues remaining with the catalyst, the column hold-up, the amount lost in transfers and other unavoidable losses in recovery.

It is clear from the above comparative data that the new process using the hydrated ferric chloride as catalyst gives unexpectedly higher yields as well as much greater selectivities (high isomer ratios) for the preferred 2,5-dibromo-p-xylene isomer.

What is claimed is:

1. Selective bromination process for 2,5-dibromo-p-xylene which comprises contacting p-xylene with bromine at a temperature of about −20°C. to 40°C. in the presence of from about 0.25 to about 5.0 mole percent based on the bromine of a hydrated iron containing catalyst having from about two to about six molecules of water per atom of iron present in the catalyst.

2. The process of claim 1 in which the hydrated iron containing catalyst is a hydrated ferric halide.

3. The process of claim 2 in which the hydrated ferric halide is ferric chloride trihydrate.

4. The process of claim 1 in which the iron containing catalyst is a hydrated ferric nitrate.

5. The process of claim 1 in which the iron containing catalyst is a hydrated ferric sulfate.

6. The process of claim 2 in which the bromine to p-xylene ratio is maintained in the range of 1.8 up to 2.4.

7. The process of claim 2 in which the crude bromination product is washed, the monobromo-p-xylene is stripped off, and the residue recovered is substantially pure 2,5-dibromo-p-xylene.

8. The process of claim 2 in which the crude bromination product is distilled under reduced pressure to obtain 2,5-dibromo-p-xylene.

9. The process of claim 1 which comprises carrying out the bromination in the presence of monobromo-p-xylene.

10. A continuous selective bromination process for 2,5-dibromo-p-xylene according to claim 1 in which the monobromo-p-xylene is separated and recycled to the reaction process.

11. The process of claim 7 in which the 2,5-dibromo-p-xylene product is contacted with at least one alkanol of 1–4 carbon atoms to remove impurities by selective dissolution and thereafter pure 2,5-dibromo-p-xylene is recovered in high yield.

12. As an additional feature, the process of claim 8 in which the 2,5-dibromo-p-xylene product is treated with at least one aliphatic alcohol of 1–4 carbon atoms to remove impurities and thereafter pure 2,5-dibromo-p-xylene is recovered in high yield.

* * * * *